US009241846B2

(12) United States Patent
Melki

(10) Patent No.: US 9,241,846 B2
(45) Date of Patent: Jan. 26, 2016

(54) MALE HYGIENE DEVICE

(75) Inventor: Vilyam Melki, Upplands V•sby (SE)

(73) Assignee: Prevent Hygiene Products AB, Sodertalje (SE)

( * ) Notice: Subject to any disclaimer, the term of this patent is extended or adjusted under 35 U.S.C. 154(b) by 240 days.

(21) Appl. No.: 13/877,917

(22) PCT Filed: Sep. 28, 2011

(86) PCT No.: PCT/SE2011/051155
§ 371 (c)(1),
(2), (4) Date: Jun. 13, 2013

(87) PCT Pub. No.: WO2012/047151
PCT Pub. Date: Apr. 12, 2012

(65) Prior Publication Data
US 2013/0253459 A1    Sep. 26, 2013

(30) Foreign Application Priority Data

Oct. 8, 2010    (SE) ...................... 1051055

(51) Int. Cl.
| A61F 13/471 | (2006.01) |
| A61F 13/56 | (2006.01) |
| A61F 5/40 | (2006.01) |
| A61F 5/453 | (2006.01) |
| A61F 13/80 | (2006.01) |
| A61F 13/82 | (2006.01) |

(52) U.S. Cl.
CPC ............... *A61F 13/5611* (2013.01); *A61F 5/40* (2013.01); *A61F 5/453* (2013.01); *A61F 13/471* (2013.01); *A61F 13/80* (2013.01); *A61F 13/82* (2013.01)

(58) Field of Classification Search
CPC ......... A61F 13/471; A61F 13/80; A61F 5/40; A61F 5/453
See application file for complete search history.

(56) References Cited

U.S. PATENT DOCUMENTS

| 1,989,686 | A |   | 2/1935 | Deutsch |
| 2,713,340 | A |   | 7/1955 | Meminger |
| 4,505,707 | A | * | 3/1985 | Feeney ........................ 604/393 |
| 4,668,229 | A | * | 5/1987 | Fago et al. ................... 604/327 |
| 5,094,234 | A |   | 3/1992 | Searcy |

(Continued)

FOREIGN PATENT DOCUMENTS

| CN | 201026253Y Y | 2/2008 |
| JP | 2010150740 A | 7/2010 |
| JP | 3083216 | 10/2010 |

OTHER PUBLICATIONS

Complete set of drawings as originally filed in U.S. Appl. No. 11/222,606 (Girgen et al., US 2008/0108864).*

(Continued)

*Primary Examiner* — Susan Su
(74) *Attorney, Agent, or Firm* — Harness, Dickey & Pierce, PLC

(57) ABSTRACT

A one-piece hygiene band (100) for use by a male to absorb moisture is provided. The hygiene band comprises an absorbent material and has at least one interconnection means (105) at a first portion (106) of the hygiene band arranged for allowing an interconnection between the first portion and a second portion (108) of the hygiene band such that a loop (114) of the hygiene band may be formed for being provided around the genitals (116) of the male. At least a segment (112) of the hygiene band is arranged for being provided between the buttocks (120) of the male.

10 Claims, 3 Drawing Sheets

(56) References Cited

U.S. PATENT DOCUMENTS

| | | | |
|---|---|---|---|
| 6,593,509 B1* | 7/2003 | Nitenson | 604/358 |
| 7,928,279 B2* | 4/2011 | Rosenberg | 602/48 |
| 2004/0030307 A1 | 2/2004 | Nitenson | |
| 2005/0268380 A1 | 12/2005 | Sovell | |
| 2008/0108864 A1* | 5/2008 | Girgen et al. | 600/41 |
| 2013/0291879 A1* | 11/2013 | Matsuda | 128/885 |
| 2014/0343521 A1* | 11/2014 | Melki | 604/359 |

OTHER PUBLICATIONS

International Search Report for PCT/SE2011/051155, mailed Jan. 26, 2012; ISA/SE.

First Office Action for Chinese Patent Application 201180055937.3 (with English translation).

\* cited by examiner

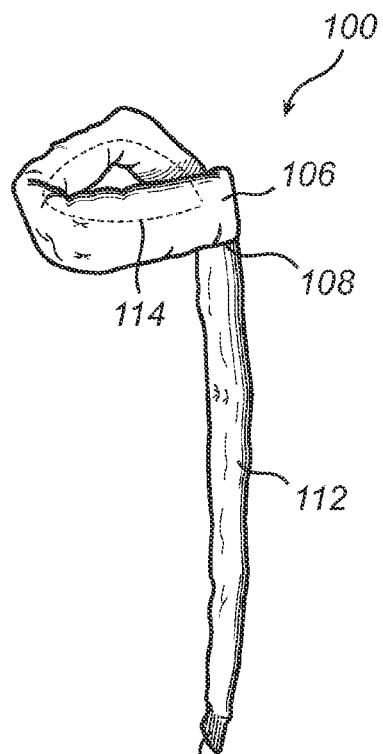
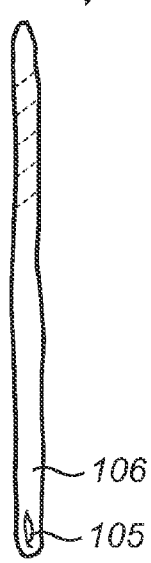
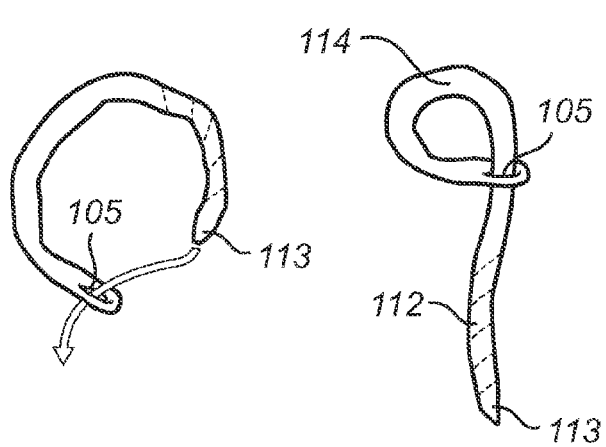
Fig. 3
Fig. 4a   Fig. 4b   Fig. 4c

MALE HYGIENE DEVICE

CROSS-REFERENCE TO RELATED APPLICATIONS

This application is a 371 U.S. National Stage of International Application No. PCT/SE2011/051155, filed on Sep. 28, 2011, which claims priority to Swedish Patent Application No. 1051055-0, filed Oct. 8, 2010, the contents of which are hereby incorporated by reference in their entirety as if fully set forth herein.

FIELD OF THE INVENTION

The present invention relates to a male hygiene device for medicinal, hygiene and/or aesthetic purposes.

BACKGROUND OF THE INVENTION

Males of any age may be affected by irritations and/or infections in or around the crotch, wherein these irritations may appear as itching, burning sensations and/or pain in the groin area, (uro)genital area, thigh skin folds, anus (perianal area) and/or between the buttocks (intergluteal area). Affected areas may appear on the thigh and/or scrotum side as red, tanned, or brown areas, with flaking, rippling, peeling, or cracking skin, wherein the condition may result in a general discomfort or pain. Moreover, dermal body fluid discharges may appear in the crotch area due to infections.

The crotch area may often be exposed to a warm, damp environment from tight, sweaty clothing such as underwear and/or jock straps. This may contribute to e.g. the cultivation of fungus, which may cause crotch itches. To prevent the occurrence of crotch irritations and/or infections, it has been suggested to keep the groin area clean and dry by e.g. drying off thoroughly after bathing, putting on dry clothing immediately after swimming or perspiring, not sharing clothing or towels with others, showering immediately after athletic activities, wearing loose cotton underwear, avoiding tight-fitting clothing and/or using antifungal, antibacterial powders and/or ointments in the groin area.

However, the above-mentioned actions to prevent e.g. crotch itch and/or discomforts in the crotch area may be tedious and inconvenient. Therefore, there is a wish to more conveniently inhibit the occurrence of crotch itches, irritations and/or infections.

In patent document US2004/0030307 A1, an absorbent article is provided for a male user for absorbing moisture at the scrotum. The absorbent article comprises an elongated soft pad made of an absorbent material. The article is sized to wrap around the rear of the scrotum and lie against the inner thigh of the user. A strap is connected to the ends of the pad for extending around the waist of the user, thereby holding the pad in place about the scrotum and against the inner thigh.

However, there are problems related to this article, as the construction of the article is inconvenient and obstructive for the user.

SUMMARY OF THE INVENTION

It is an object of the present invention to mitigate the above problems and to provide a more convenient device for medicinal, hygiene and/or aesthetic purposes related to the male crotch area.

This and other objects are achieved by providing a device having the features defined in the independent claim. Preferred embodiments are defined in the dependent claims.

Hence, according to a first aspect of the present invention, there is provided a one-piece hygiene band for use by a male to absorb moisture, wherein the hygiene band comprises an absorbent material. The hygiene band has at least one interconnection means at a first portion of the hygiene band. The interconnection means is arranged for allowing an interconnection between the first portion and a second portion of the hygiene band such that a loop of the hygiene band is formed for being provided around the genitals of the male. At least a segment of the hygiene band is arranged for being provided between the buttocks of the male.

Thus, the present invention is based on the idea of providing a one-piece hygiene band for men for absorbing moisture in the urogenital, perianal and/or intergluteal regions. A loop of the hygiene band is formed for being provided around the male genitals, wherein at least a segment of the hygiene band is arranged for being provided between the buttocks of the male.

An advantage of the present invention is that the hygiene band may prevent and/or treat irritations, eczematous rashes, skin eruptions and/or general discomforts in the urogenital, perianal and/or intergluteal regions. Hence, the prophylactic aspect of the hygiene band may prevent the occurrence of e.g. itches, infections, eczema and/or haemorrhoid-related ailments in the mentioned regions.

Another advantage of the present invention is that the hygiene band may prevent and/or treat infections in the urogenital, perianal and/or intergluteal regions, wherein these infections may be caused by infectious agents such as virus, bacteria, and/or fungus. Hence, in a medical aspect, the hygiene band may prevent diseases caused by these infectious agents.

Furthermore, as the hygiene band is arranged for absorbing moisture from the urogenital, perianal and/or intergluteal regions, the hygiene band also provides advantages in a hygienic aspect. The moisture-absorbing material of the hygiene band may reduce smells from the mentioned crotch regions, thereby increasing the health, comfort, and the sense of freshness, cleanliness and well-being of the user.

Another advantage of the present invention is that the hygiene band may at least partly separate skin contact between the male genitals, the buttocks, and/or a skin contact between the male genitals and the crotch. In other words, the male hygiene band may at least partly avoid skin contact between the penis and the scrotum, between the scrotum and the crotch, and/or the skin contact between the buttocks. By avoiding skin contact between the organs in the crotch region, the hygiene band may relieve irritations, rashes and/or discomforts in the urogenital, perianal and/or intergluteal regions.

A further advantage of the present invention is that the hygiene band is easily applied around the genitals and between the buttocks, wherein the loop is readily provided around the genitals, and the remnant at least a segment of the hygiene band is easily provided between the buttocks. Furthermore, the hygiene band is easily adjusted regarding the size of the loop of the hygiene band. For example, a user having a relatively small scrotum and/or penis, a relatively small loop of the hygiene band may be formed. In contrast, a relatively large loop of the hygiene band may be formed for a user with a relatively large scrotum and/or penis.

Another advantage of the present invention is that the hygiene band, in one-piece, results in an even more convenient hygiene band compared to arrangements wherein two or more pieces, e.g. waistbands, belts and/or girdles, have to be attached by the user. Arrangements of the latter kind lead to a cumbersome and awkward operation, whereas the one-piece hygiene band of the present invention is easily and conveniently applied.

By its relative simplicity, the hygiene band further provides the advantage of being simple and inexpensive to fabricate. Furthermore, as the hygiene band is soft and supple, it is convenient to apply around the genitals, comfortable, and easily portable with or without underwear. The lithe hygiene band may provide a form which adapts to the anatomy of the user, further contributing to the comfort of the user. Moreover, when not in use, the hygiene band is easily portable in e.g. a bag.

Another advantage of the present invention is that hygiene band may be disposable. Hence, after use, the hygiene band may be rejected, and a new hygiene band may be applied. Alternatively, the hygiene band may be washed by hand or in a washing machine, such that the hygiene band may be reused.

Another advantage of the present invention is that the hygiene band may emphasize the genitals of the male, i.e. the penis and/or scrotum when the hygiene band is provided around the genitals. In other words, the hygiene band may support, lift and/or push up the genitals, thereby providing a more esthetic profile with respect to the body silhouette.

Another advantage of the present invention is that the hygiene band, when provided around the genitals and between the buttocks of said male, may stay in place, even though the user may perform physical activities and/or exercises such as running, cycling, playing football, etc. The hygiene band may stay in place even in cases when the user, wearing the hygiene band, wears no underwear.

The term "band" may here be construed as an elongated band, string, strap, or the like. The band may be soft, supple and/or easily flexible, such that e.g. a loop of the band may be easily formed. Furthermore, the band may be elastic in the elongated direction of the band, or, in contrary, inelastic in the same direction.

The term "moisture" may here predominantly be construed as sweat and/or dermal body fluid discharges. The moisture may occur in the crotch region due to e.g. physical activity, nervousness, heat, infections, etc. However, other body liquids such as e.g. traces of urine, semen and/or blood may be comprised within the meaning of the term.

The hygiene band comprises an absorbent material, which may be substantially any material which has high absorption properties. Furthermore, the hygiene band may comprise e.g. textiles for reasons of hygiene band structure and/or re-utilization of the hygiene band, by means of washing.

The hygiene band has at least one interconnection means at a first portion of the hygiene band. By the term "interconnection means", it is here meant any means for an interconnection and/or fastening. For example, the interconnection means may be provided within the hygiene band, such as a hole, an aperture, or the like, arranged for receiving a portion of the hygiene band. Alternatively, the interconnection means may extend from the hygiene band in form of a loop, a strap, or the like.

A further example of the interconnection means may be a chemical adhesive such as glue, or the like. Alternatively, the interconnection means may provide an interconnection such as a hook-and-loop fastener, or the like.

The first portion of the hygiene band at which the interconnection means is provided may be, substantially, any portion of the hygiene band. For example, the first portion, which may be a point, a section, a segment, or the like, of the hygiene band, may be provided e.g. in the middle of the hygiene band, between the middle and an end of the hygiene band, or at an end of the hygiene band.

The interconnection means is arranged for allowing an interconnection between the first portion and a second portion of the hygiene band such that a loop of the hygiene band is formed. Hence, the first portion and the second portion of the hygiene band are separate portions of the hygiene band, defining a starting point and an end point of the loop when a loop of the hygiene band is formed. In other words, the second portion of the hygiene band may be interconnected to the interconnection means of the first portion such that a loop is formed. For example, if the interconnection means is a hole, an aperture, a loop, a strap, or the like, arranged for receiving a portion of the hygiene band, the second portion of the hygiene band may be substantially any portion of the hygiene band, which, when the interconnection means receives a portion of the hygiene band, defines the loop together with the first portion.

The loop of the hygiene band is formed for being provided around the genitals of the male. Hence, the loop of the hygiene band is formed for encircling the penis and/or scrotum of the male. The loop may be provided around the genitals along the crotch, i.e. around the base of the penis and between the scrotum and the crotch. Alternatively, the loop may be provided merely around the penis, such that the loop is provided e.g. around the penis and between the penis and the scrotum. Analogously, the loop may be provided merely around the scrotum.

At least a segment of the hygiene band is arranged for being provided between the buttocks of the male, i.e. in the intergluteal region. By "segment", it is here meant a portion or a part of the hygiene band which may be a portion of the loop, or a portion which is separate from the loop. For example, a loop of the hygiene band may be formed for being provided around the genitals of the male, and at least a segment (hereafter denoted segment) of the hygiene band may then be arranged between the buttocks of the male. In other words, from the loop of the hygiene band which is formed around the genitals, the continuation portion or portions of the hygiene band may be provided between the buttocks.

According to an embodiment of the present invention, the segment of the hygiene band may be a segment of the hygiene band which is separate from the loop of the hygiene band. In other words, in this embodiment, there is no overlap between the segment of the hygiene band being arranged for being provided between the buttocks of the male and the loop of the hygiene band which is formed for being provided around the genitals of the male. For example, the segment of the hygiene band may be a portion of the hygiene band which is remnant when the loop of the hygiene band is formed. In other words, when the loop of the hygiene band is formed, a segment of a first end of the hygiene band and/or a segment of a second end of the hygiene band may be remnant from the loop of the hygiene band, and be provided between the buttocks.

In the case of one segment of the hygiene band being remnant of the hygiene band when the loop of the hygiene band is formed, the user may in a straightforward way place the segment between the buttocks. Hence, from the loop of the hygiene band provided around the genitals, the hygiene band continues into the remnant segment which may be provided between the buttocks.

In the case of two segments of the hygiene band being remnant of the hygiene band when the loop of the hygiene band is formed, the user may provide the two segments between the buttocks e.g. simply side-by-side, or by plaiting the two segments.

According to an embodiment of the present invention, the first portion of the hygiene band may be provided at a first end of the hygiene band. In other words, the first portion of the hygiene band, wherein the first portion has at least one interconnecting means, may be provided close to, or immediately adjacent, one end of the hygiene band. In the present embodiment of the invention, the loop of the hygiene band may be formed from the first end of the hygiene band. In other words, when the first and the second portions of the hygiene band interconnect to form the loop, only a relatively small/short portion or segment such as a stump, a bit, a shred, or the like, of the hygiene band is left of the first end of the hygiene band.

In the present embodiment of the invention, the shape of the hygiene band, when the loop of the hygiene band is formed, may resemble that of a lasso, or the like. From the loop, one segment from the hygiene band becomes remnant, and the segment may be provided between the buttocks.

An advantage of the present embodiment of the invention is that the loop of the hygiene band becomes easily formed. Furthermore, as the first portion of the hygiene band is provided at a first end of the hygiene band, the occurrence of portions of the hygiene band which may be redundant and/or are not primarily intended to be used for the purposes of the hygiene band, may be avoided.

According to an embodiment of the present invention, the at least one interconnection means may be a hole, an aperture, a loop, a strap, or the like. For example, if the at least one interconnection means is a hole or an aperture, a loop of the hygiene band may be formed by passing a second end of the hygiene band through the hole/aperture. In other words, the second end may be passed through the hole in a direction substantially perpendicular to the elongation of the hygiene band at the first portion. Alternatively, if the at least one interconnection means is a loop or a strap, a loop of the hygiene band may be formed by passing a second end through the loop/strap, i.e. in a direction substantially parallel to the elongation of the hygiene band at the first portion.

An advantage with the present embodiment of the invention is that no other auxiliary material and/or chemical fastening means, such as glue, may be necessary for the interconnection between the first portion and the second portion to form the loop. Hence, the embodiment may provide an even easier application for the user. Further, the present embodiment may be beneficial for the avoidance of e.g. itching and/or discomfort from the auxiliary material/fastening means. Another advantage with the present embodiment of the invention is that a hygiene band without auxiliary material/fastening means may be preferred regarding a recycling aspect of the hygiene band.

According to an embodiment of the present invention, at least a portion of the segment of the hygiene band may be provided with at least one perforation arranged for allowing an adjustment of the length of the hygiene band. For example, the at least one perforation may be provided substantially perpendicular to the elongation of the hygiene band such that the length of the hygiene band may be adjusted by tearing off a portion of the segment of the hygiene band.

The present embodiment is advantageous regarding the adaptation of the hygiene band related to the individual size of the urogenital, perianal and/or intergluteal regions of the user and/or the individually preferred use of the hygiene band. As an example, a user having a relatively small scrotum, penis and/or intergluteal passage may need to adjust the length of the hygiene band if it is too long. This may also be the case if the user prefers the loop of the hygiene band provided around the genitals to be tight, thereby leaving a relatively long segment to be provided between the buttocks. Alternatively, a user having a relatively large scrotum, penis and/or intergluteal passage may prefer only a small adjustment the length of the hygiene band, or no adjustment at all. In any case, the at least one perforation provides a simple and intuitive way of individual user size adjustment by removal of a portion of the segment of the hygiene band.

For example, the portion of the segment of the hygiene band being provided with the at least one perforation may approximately be a fifth of the entire length of the hygiene band. Hence, the length of the hygiene band may be reduced by up to approximately 20%. However, it should be noted that the at least one perforation may easily be provided along a longer length of the hygiene band, e.g. such that the length of the hygiene band may be reduced by up to approximately 50%.

According to an embodiment of the present invention, the segment of the hygiene band may be provided with an adhesive material for fastening the segment of the hygiene band between the buttocks of the male. An advantage with the present embodiment is that the segment of the hygiene band may more easily stick or attach to the buttocks of the user compared to the case when no adhesive material is applied, such that the hygiene band is even more likely to stay in place between the buttocks. This may especially be advantageous during any kind of physical activity or exercise of the user such as running, cycling, weight training, playing football, etc.

Alternatively, the segment of the hygiene band may be provided with an adhesive material for adhesion of at least a portion of the hygiene band to an article of clothing, e.g. the underwear of the user.

According to an embodiment of the present invention, the absorbent material may be made of, or a combination of, cellulose, cellulose fluff, wood fluff, cotton, or the like, or a combination thereof. Hence, the absorbent material may comprise any material, or any combination of material, which is moisture absorbing.

An advantage with the absorbent materials proposed for the hygiene band is that they may absorb and retain extremely large amounts of a moisture relative to the mass of the hygiene band material used.

A further advantage of the absorbent materials proposed in the present embodiment is that the materials are soft and pliable, providing comfort for the user. Furthermore, the mentioned absorbent materials provide the ability of the hygiene band to be easily folded and transported, when not in use.

According to an embodiment of the present invention, the hygiene band may further comprise a medicinal agent and/or deodorant.

By the term "medicinal agent", it is here meant any medicament for the cure, treatment or prevention of disease. More specifically, the medicinal agent may be a liquid, a gel, an ointment, or the like, such that at least a portion of the hygiene band may be impregnated with the medical agent. By the term "deodorant", it is here meant any substance for eliminating or reducing odor caused by the bacterial breakdown of perspiration.

For example, at least a portion of the absorbent material of the hygiene band may be impregnated with a medicinal agent and/or deodorant.

An advantage with the embodiment of the present invention is that the medicinal agent and/or deodorant may further prevent and/or treat irritations, infections, eczematous rashes, eruptions and/or general discomforts in the urogenital, perianal and/or intergluteal regions.

A further advantage with the embodiment of the present invention is that the medicinal agent and/or deodorant may further inhibit or reduce odor and/or provide a pleasant scent, which may increase the sense of freshness and/or well-being of the user.

According to an embodiment of the present invention, the width of the hygiene band may be larger than the thickness of the hygiene band. In other words, the elongated band may be relatively oval or flat. An advantage with the embodiment of the present invention is that when forming the loop of the hygiene band to be applied around the genitals of the user, the width of the band may abut the groin on one side and the scrotum on the other side. By this, larger areas of the hygiene band may be provided against the groin and the scrotum compared to a hygiene band being e.g. round. Moreover, if the segment of the hygiene band which is arranged for being provided between the buttocks of the user may be relatively oval, the width of the segment may be provided towards the buttocks. By this, the segment may provide e.g. a larger area of skin separation between the buttocks.

According to an embodiment of the present invention, the length of the hygiene band may be within 40-80 cm, such as within 50-70 cm. The mentioned intervals of the length of the hygiene band may represent a sufficiently long length for the formation of a loop of the hygiene band, wherein a segment of the hygiene band is arranged for being provided between the buttocks of the male. For example, a relatively long length of the hygiene band may be preferred by a user having a relatively large scrotum, penis and/or intergluteal passage such that the hygiene band may provide a sufficient length around the genitals and between the buttocks of the user. However, if the length of the hygiene band is considered by the user to be too long, an adjustment is possible by means of the at least one perforation such that a portion of the segment of the hygiene band may be torn off. At the same time, the mentioned intervals of the length of the hygiene band may represent a hygiene band which is sufficiently short such that the hygiene band may be easily portable in e.g. a bag.

According to an embodiment of the present invention, the width of the hygiene band may be within 0.5-5 cm, such as within 1-3 cm. The mentioned intervals of the width of the hygiene band may provide a hygiene band which is sufficiently small in width such that the hygiene band is supple, conveniently applied around the male genitals and between the buttocks, and easily portable, still being sufficiently large in width such that the hygiene band may be suitable for its purposes, i.e. absorbing moisture.

BRIEF DESCRIPTION OF THE DRAWINGS

These and other aspects of the present invention will now be described in more detail, with reference to the appended drawings showing a currently preferred embodiment of the invention, wherein:

FIGS. 2-3 are views of the hygiene band when a loop of the hygiene band has been formed, FIGS. 4a)-c) are schematic illustrations of the forming of the loop of the hygiene band.

DETAILED DESCRIPTION

In the following description, the present invention is described with reference to a hygiene band for use by a male to absorb moisture.

Figure 1:
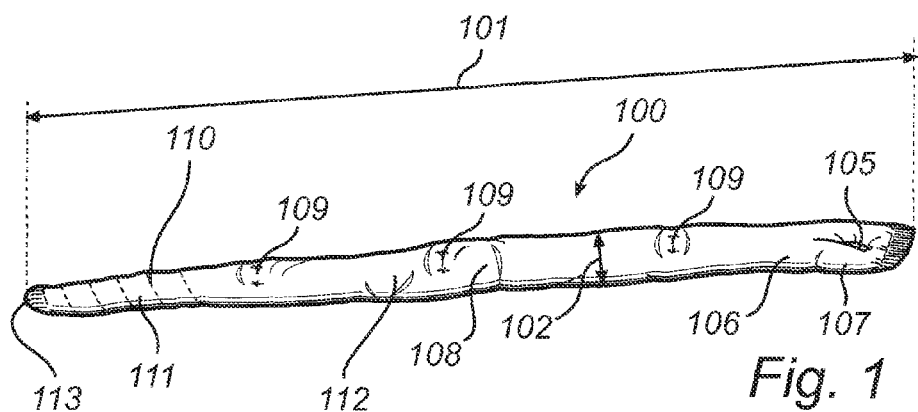
FIG. 1 is a view of the hygiene band in an elongated position.

FIG. 1 is a view of the hygiene band 100 in an elongated position, wherein the length 101 of the hygiene band 100 is approximately 50-70 cm. Furthermore, the width 102 of the hygiene band 100 is approximately 1-3 cm. The thickness of the hygiene band 100 is generally somewhat smaller than the width 102, yielding a substantially flat or oval shape of the hygiene band 100. However, the hygiene band 100 may also be realized in an substantially round shape.

The hygiene band 100 may comprise an absorbent material such as cellulose, cellulose fluff, wood fluff, cotton, or the like, or a combination thereof, arranged for absorbing moisture.

The hygiene band 100 has an interconnection means in the form of a hole/aperture 105 at a first portion 106 of the hygiene band 100, wherein the hole 105 is slightly elongated parallel to the length 101 of the hygiene band 100. More specifically, for the embodiment of the hygiene band 100 as shown in FIG. 1, the first portion 106 is provided at a first end 107 of the hygiene band 100, i.e. the hole 105 is provided close to the end of the hygiene band 100. The hole 105 is arranged for allowing an interconnection between the first portion 106 and a second portion 108 of the hygiene band 100. The second portion 108 may be provided substantially anywhere along the length 101 of the hygiene band 100, but is in FIG. 1 provided approximately in the middle of the hygiene band 100.

In the embodiment of the hygiene band 100 in FIG. 1, three pairs of perforations 109 are symmetrically distributed along the length 101 of the hygiene band 100. The perforations 109 may be provided for preventing the occurrence of air entrapment inside the hygiene band 100.

At least one perforation 110 is arranged at a portion 111 of a segment 112 of the hygiene band 100 for allowing an adjustment of the length 101 of the hygiene band 100. The at least one perforation 110 is in FIG. 1 provided in a spiral extending from a second end 113 of the hygiene band 100 into approximately a fifth of the entire length 101 of the hygiene band 100. Alternatively, the at least one perforation 110 may be provided as a plurality of perforations 110 around the hygiene band 100, perpendicular to the elongation of the hygiene band 100 and separated in the direction of the elongation of the hygiene band 100.

Figure 2:
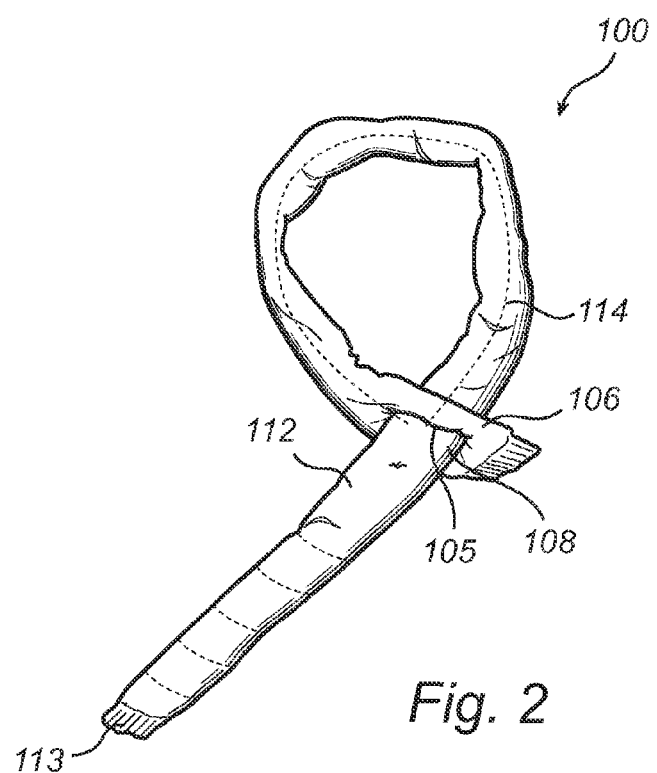

FIG. 2 is a top view of the hygiene band 100 when the second end 113 of the hygiene band 100 has been passed through the hole 105 at the first portion 106 of the hygiene band 100. Here, the interconnection between the first portion 106 and the second portion 108 of the hygiene band 100 defines a loop 114. In other words, the loop 114 starts from the first portion 106 and ends at the second portion 108. Consequently, the second portion 108 may be substantially anywhere along the length of the hygiene band 100, as the variable loop 114 is defined by the location of the second portion 108.

The loop 114 is arranged for being provided around the genitals of the male user, i.e. penis and/or scrotum. As the loop 114 may be made smaller or larger, the user may adapt the size of the loop 114 of the hygiene band 100 to his penis/scrotum size and/or with respect to his comfort preferences. The segment 112 of the hygiene band 100 is arranged for being provided between the buttocks of the user. The segment 112 may be any portion of the hygiene band 100 between the second end 113 and the second portion 108, i.e. that any portion defined by the second end 113 and the second portion 108 may be provided between the buttocks of the user. In other words, the segment 112 may be separate from the loop 114 of the hygiene band 100. Alternatively, the segment 112 may e.g. be a portion of the loop 114 of the hygiene band 100, i.e. that also a portion of the loop 114 may be provided between the buttocks.

FIG. 3 is a side view of the hygiene band 100 when the second end 113 of the hygiene band 100 has been passed through the hole (not shown) at the first portion 106 of the hygiene band 100 to form the loop 114. Compared to the realization of the hygiene band 100 as shown in FIG. 2, the hygiene band 100 in FIG. 3 has been tightened such that the circumference of the loop 114 has approximately the same length as the segment 112 of the hygiene band 100 between the interconnection of the first portion 106 and the second portion 108 and the second end 113.

FIG. 4 is a schematic illustration of the forming of the loop 114 of the hygiene band 100. In FIG. 4a), the hygiene band 100 is depicted in its elongated form, wherein the hole 105 is provided at the first portion 106 of the hygiene band 100. In FIG. 4b), the forming of the loop 114 of the hygiene band 100 has been initiated, wherein the hygiene band 100 almost forms a circle and wherein the second end 113 of the hygiene band 100 points towards the hole 105. In FIG. 4c), the second end 113 of the hygiene band 100 has passed through the hole 105 of the hygiene band 100, thereby forming the loop 114 arranged for being provided around the genitals of a male, wherein the segment 112 of the hygiene band 100 is arranged for being provided between the buttocks of the male.

Figure 5:
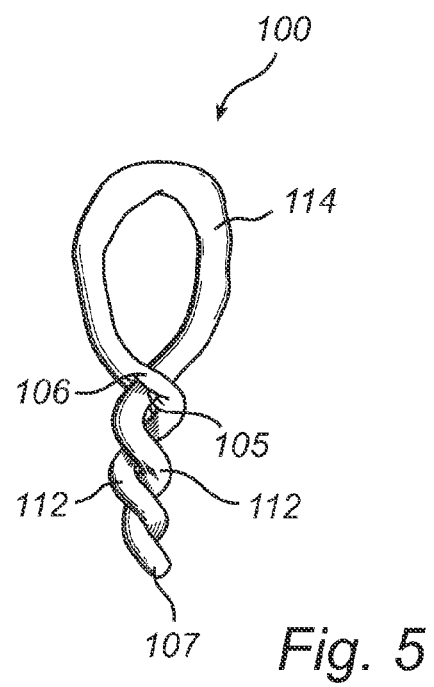
FIG. 5 is a schematic illustration of an alternative embodiment of the hygiene band.

FIG. 5 is a schematic illustration of the hygiene band 100, wherein an alternative embodiment of the present invention is shown. In FIG. 5, the hole 105 is provided at the first portion 106 which is provided approximately between the first end 107 and the middle of the hygiene band 100. In this way, when the loop 114 of the hygiene band 100 has been formed, two segments 112 of the hygiene band 100 are formed for being provided between the buttocks of the male. The two segments 112 may be provided between the male buttocks e.g. simply side-by-side. Alternatively, as shown in FIG. 5, the two segments 112 may be plaited.

Figure 6:
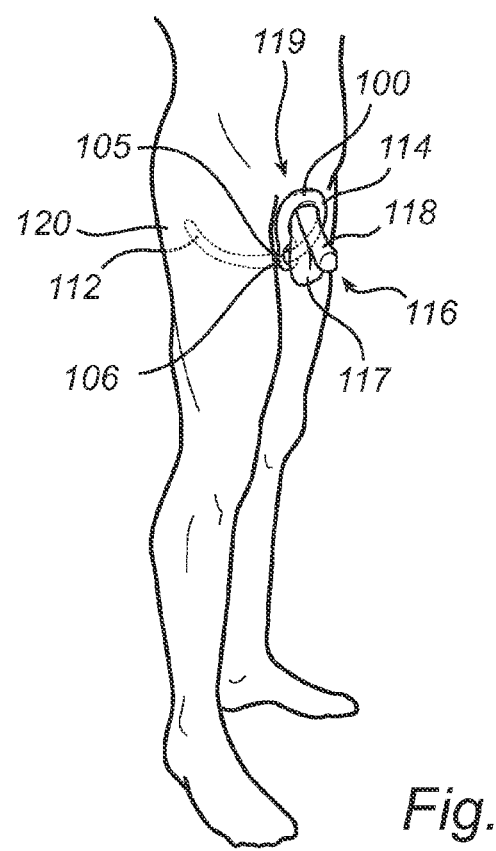
FIG. 6 is a schematic illustration of the hygiene band provided on a male user.

FIG. 6 is a schematic illustration of the hygiene band 100 provided on a male user. The loop 114 of the hygiene band 100 is provided around the male genitals 116, i.e. the scrotum 117 and penis 118, of the user. More specifically, as depicted in FIG. 6, the loop 114 of the hygiene band 100 elongates from the first end (first portion 106) of the hygiene band 100, between the genitals 116 and the lower abdomen 119, i.e. around the base of the penis 118 and between the scrotum 117 and the crotch, and back through the hole 105 at the first end (first portion 106) of the hygiene band 100. The segment 112 of the hygiene band 100, i.e. at least a portion of the remnant of the hygiene band loop 114, may be provided between the buttocks 120 of the user.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

For example, the hygiene band 100 may have a flatter shape than that depicted in the figures, such that the hygiene band 100 may take on the shape of a pad, or the like. Furthermore, the hole 105 may instead be circular or rectangular and/or be smaller or larger compared to the embodiments in the figures.

As an alternative aspect of the present invention, the interconnection means may be a means separable from the hygiene band 100 such as a ring, or the like, arranged for receiving at least a portion of the hygiene band 100. For example, the interconnection means between the first portion 106 and the second portion 108 of the hygiene band 100 may be a ring which is thread on the two segments 112 of the hygiene band 100. In this alternative aspect of the invention, the size of the loop 114 may be adjusted by the ring. For example, if the user prefers a more tight fit of the loop 114 around the genitals 116, the ring may be brought upwards, thereby decreasing the size of the loop 114.

The invention claimed is:

1. A one-piece hygiene band for use by a male to absorb moisture, said hygiene band comprising:
   an absorbent material and having at least one interconnection means at a first portion of said hygiene band arranged for allowing an interconnection between said first portion and a second portion of said hygiene band such that a loop of said hygiene band is formed for being provided around the genitals of said male,
   wherein at least a segment of said hygiene band is arranged for being provided between the buttocks of said male; and
   wherein at least a portion of said at least a segment of said hygiene band is provided with at least one perforation arranged for allowing an adjustment of the length of said hygiene band by tearing off a portion of said at least a segment of said hygiene band.

2. The one-piece hygiene band as claimed in claim 1, wherein said at least a segment of said hygiene band is at least a segment of said hygiene band being separate from said loop of said hygiene band.

3. The one-piece hygiene band as claimed in claim 1, wherein said first portion of said hygiene band is provided at a first end of said hygiene band.

4. The one-piece hygiene band as claimed in claim 1, wherein said at least one interconnection means is a hole, an aperture, a loop, or a strap.

5. The one-piece hygiene band as claimed in claim 1, wherein said at least a segment of said hygiene band is provided with an adhesive material for fastening said at least a segment of said hygiene band between said buttocks of said male.

6. The one-piece hygiene band as claimed in claim 1, wherein said absorbent material is made of cellulose, cellulose fluff, wood fluff, cotton, or a combination thereof.

7. The one-piece hygiene band as claimed in claim 1, further comprising a medicinal agent and/or deodorant.

8. The one-piece hygiene band as claimed in claim 1, wherein the width of said hygiene band is larger than the thickness of said hygiene band.

9. The one-piece hygiene band as claimed in claim 1, wherein the length of said hygiene band is within 40-80 cm.

10. The one-piece hygiene band as claimed in claim 1, wherein the width of said hygiene band is within 0.5-5 cm.

* * * * *